(12) United States Patent
Rapp et al.

(10) Patent No.: US 7,432,103 B2
(45) Date of Patent: Oct. 7, 2008

(54) METHODS OF PROTEIN PRODUCTION IN CELL LINES

(75) Inventors: Jeffrey C. Rapp, Athens, GA (US); Stephen H. Parker, Jefferson, GA (US); Markley C. Leavitt, Watkinsville, GA (US); Dawn M. Eberhardt, Danielsville, GA (US); Leandro Christmann, Watkinsville, GA (US); Alex J. Harvey, Athens, GA (US)

(73) Assignee: AviGentics, Inc., Athens, GA (US)

( * ) Notice: Subject to any disclaimer, the term of this patent is extended or adjusted under 35 U.S.C. 154(b) by 0 days.

(21) Appl. No.: 12/012,387

(22) Filed: Feb. 1, 2008

(65) Prior Publication Data

US 2008/0145861 A1 Jun. 19, 2008

Related U.S. Application Data

(62) Division of application No. 11/454,399, filed on Jun. 16, 2006, now Pat. No. 7,351,582.

(60) Provisional application No. 60/692,036, filed on Jun. 17, 2005.

(51) Int. Cl.
*C12N 15/02* (2006.01)
*C12N 5/02* (2006.01)
*C12N 15/00* (2006.01)

(52) U.S. Cl. .................. 435/325; 435/449; 435/455
(58) Field of Classification Search .............. 435/325, 435/455, 499
See application file for complete search history.

(56) References Cited

U.S. PATENT DOCUMENTS 6,730,822 B1    5/2004    Ivarie et al.
7,351,582 B2*    4/2008    Rapp et al. .................. 435/325

OTHER PUBLICATIONS

Definition of immortal, Merriam-Webster dictionary online, 2007.
Definition of immortalise, Online Medical Dictionary, 2007.
Gaub et al., The chicken ovalbumin promoter is under negative control which is relieved by steroid hormones, EMBO vol. 6(8):2313-20 (1987).
De Buck et al., Tubular Glands of the Isthmus Are the Predominant Coloniza Site of Salmonella Enteritidis in the Upper Oviduct of Laying Hens, Poultry Sci, 83:352-58, (2004).

* cited by examiner

*Primary Examiner*—Michael C. Wilson
(74) *Attorney, Agent, or Firm*—Kyle D. Yesland (57) ABSTRACT

The present invention relates to cells that can be passaged in culture and can be used for, among other things, promoter assays and the production of heterologous proteins.

18 Claims, 4 Drawing Sheets

METHODS OF PROTEIN PRODUCTION IN CELL LINES

RELATED APPLICATION INFORMATION

This application is a Divisional of U.S. patent application Ser. No. 11/454,399, filed Jun. 16, 2006 now U.S. Pat. No. 7,351,582, the disclosure of which is incorporated in its entirety herein by reference, which claims the benefit of U.S. provisional application 60/692,036, filed Jun. 17, 2005.

BACKGROUND OF THE INVENTION

Recent advances have allowed for the generation of transgenic avians that express heterologous proteins in their oviduct cells. The avian oviduct contains an infundibulum, magnum, isthmus, shell gland, vagina and cloaca (Etches, Reproduction in Poultry. 1996, New York, N.Y.: CABI Publishing. 318). An ovulated ovum enters the tract through the infundibulum and continues to the magnum where the majority of egg white proteins are produced by tubular gland cells and deposited on the ova. (Palmiter, J Biol Chem, 1972. 247: 6450-61; Yu and Marquardt, Biol Reprod, 1973. 8: 283-98). Expression of the major egg white proteins is controlled by hormone responsive elements of the respective promoters (Palmiter, J Biol Chem, 1972. 247: 6450-61; Schimke et al., Basic Life Sci, 1973. 1: 123-35; Mulvihill and Palmiter, J Biol Chem, 1977. 252: 2060-8; McKnight and Palmiter, J Biol Chem, 1979. 254: 9050-8; Mulvihill and Palmiter, J Biol Chem, 1980. 255: 2085-91; Shepherd et al., J Cell Biol, 1980. 87: 142-51; Palmiter et al., J Biol Chem, 1981. 256: 7910-6; Sanders and McKnight, Endocrinology, 198.5. 116: 398-405).

Chicken oviduct cells, when stimulated by steroid hormones during egg-laying, secrete three principal polypeptides, ovalbumin, ovomucoid and lysozyme (Tsai et al., (1978) Biochemistry 17: 5773-5779). The mRNA transcript encoding ovalbumin constitutes about 50% of the total mRNA of these cells. Ovomucoid and lysozyme mRNAs contribute about 6.6% and 3.4% respectively of the total mRNA of the steroid stimulated cells. (Hynes et al. (1977) pp 932). The ability of the avian oviduct to express large amounts of various proteins makes it an attractive target for producing heterologous proteins. To date, the most common method of expressing heterologous proteins in avian oviducts is through the production of transgenic hens. In one example, transgenic hens expressing human Interferon alpha-2b (hIFN α2b) were generated (Rapp et al., Transgenic Research, 2003). Also, transgenic hens can be generated that express human monoclonal antibody in their egg white. U.S. Pat. No. 6,730,822, issued May 5, 2004, and U.S. patent application Ser. No. 10/463,980, filed Jun. 17, 2003 filed internationally as PCT/US04/01833, U.S. patent application Ser. No. 09/877,374, filed Jun. 8, 2001 filed internationally as PCT/US02/02454, U.S. patent application Ser. No. 10/679,034, filed Oct. 2, 2003 filed internationally as PCT/US02/29878, and U.S. patent application Ser. No. 10/856,218, filed May 28, 2004 filed internationally as PCT/US04/16827 disclose methods and compositions useful for the generation of transgenic avians for production of heterologous proteins. The disclosure of this issued US patent and these four pending patent applications and their corresponding PCT applications are incorporated in their entirety herein by reference. It would be useful to obtain oviduct cells, or cells having certain characteristics of oviduct cells, containing coding sequences for heterologous proteins linked to a magnum specific promoter in order to perform promoter activity studies and/or to produce heterologous proteins of commercial value (e.g., therapeutic proteins). Such promoter activity assays would be particularly useful for analyzing the activity of magnum specific promoters or fragments thereof (i.e., fragments of magnum specific promoters). For example, in many instances it is unknown which portions of magnum specific promoters, such as promoters for ovalbumin, ovomucoid, conalbumin, ovomucin and avian lysozyme proteins, are required to achieve substantial or high promoter activity in tubular gland cells. Such substantial or high promoter activity is promoter activity which is useful for the production of useful heterologous proteins in oviduct cells of transgenic avians (e.g., transgenic chickens) which have a transgene cassette in their oviduct cells containing a magnum specific promoter or fragment thereof operably linked to a DNA sequence encoding a desired protein.

Primary cultures of oviduct tissue can be generated by removing the magnum section of a sexually mature hen treated with estrogen (Sanders and McKnight, Endocrinology, 1985. 116: 398-405). The tissue can be digested with collagenase and dispase to liberate small cell clumps that are cultured for short durations. Cells collected and cultured in this manner typically die or differentiate into cells that do not produce egg white protein within three days making primary cultures of normal oviduct cells unsuitable for use in large scale in vitro production of heterologous proteins. Accordingly, improved methods for producing useful oviduct cells, or producing useful cells with characteristics of oviduct cells, are needed.

SUMMARY OF THE INVENTION

The present invention is based, at least in part, on the generation of avian cells and cell lines, such as cells and cell lines that can be obtained by fusing an immortal cell to an avian oviduct cell (e.g., a tubular gland cell). The invention contemplates such cells containing oviduct specific promoters that are operably linked to a coding sequence wherein the promoter is effective to facilitate transcription of the coding sequence. In one embodiment, the invention relates to methods of culturing under suitable nutrient conditions a cell which can be propagated in culture (e.g., a stable cell line) containing an oviduct specific promoter or a non-tissue specific promoter operably linked to a coding sequence wherein the cell comprises an immortal cell fused to an avian oviduct cell to produce a hybrid cell. The invention also relates to the progeny of hybrid cells of the invention.

In one aspect, cells of the invention are sustainable in culture for at least five or more passages (e.g., sustainable in culture for 1 to about 5 passages). In another aspect, cells of the invention are sustainable in culture for at least ten or more passages (e.g., sustainable in culture for about 2 to about 10 passages). In another aspect, cells of the invention are sustainable in culture for at least twenty or more passages (e.g., sustainable in culture for about 2 to about 20 passages). Accordingly, in one aspect, the present invention features an isolated avian cell line comprising a nucleic acid encoding a heterologous protein, wherein the cell line is sustainable in culture for at least 3 or more passages. Typically, the cell line is sustainable in culture for at least 5 passages or at least 10 passages or at least 15 passages or at least 20 passages or at least 25 passages or at least 30 passages or at least 35 passages or at least 40 passages or at least 45 passages or at least 50 passages or at least 500 passages or at least 1000 passages or at least 5000 passages or at least 10,000. In a particularly useful embodiment, the cell line is an immortal cell line capable of an unlimited number of passages.

In one aspect, cells of the invention are useful to perform reporter assays wherein the reporter assay is effective to detect or quantify the activity of a certain promoter, for example, a promoter activity assay. In one useful aspect, the reporter assay is effective to detect and/or quantify the activity of an oviduct specific promoter.

In one embodiment, the cell lines of the invention are employed to produce useful protein (e.g., useful heterologous proteins). For example, the cells of the invention can be used to produce certain human proteins. In one embodiment, the heterologous proteins produced in cell lines in accordance with the invention are pharmaceutical or therapeutic proteins. The invention contemplates isolating the protein from cells of the invention and/or from medium in which the cells are present (e.g., medium in which the cells are grown). In such case the protein produced will typically contain a signal sequence peptide as is well understood in the art.

Cell lines of the invention can employ or be used to analyze any useful promoter. Promoters contemplated for use or analysis in accordance with the present invention include constitutive promoters, which include, but are not limited to, cytomegalovirus (CMV) promoters, MDOT promoters (see, for example, US patent publication No. 2004/0019923, published Jan. 29, 2004, the disclosure of which is incorporated in its entirety herein by reference) and rous-sarcoma virus (RSV) promoters, murine leukemia virus (MLV) promoters, mouse mammary tumor virus (MMTV) promoters and SV40 promoters and functional portions of each of these promoters. Nonlimiting examples of other promoters which may be used in the present invention include, without limitation, Pol III promoters (for example, type 1, type 2 and type 3 Pol III promoters) such as H1 promoters, U6 promoters, tRNA promoters, RNase MPR promoters and functional fragments or portions of each of these promoters. Functional terminator sequences may be selected for use in the present invention, for example, in accordance with the promoter that is employed.

The invention also contemplates immortal avian cell lines, that can be passaged multiple times in cell culture and provide sustained production of heterologous polypeptides. In one embodiment, the methods of the present invention rely upon the manipulation and/or propagation of oviduct tumor cells derived from either wild-type or transgenic avians.

Avian oviduct cell lines as disclosed herein are contemplated as being derived from any suitable avian source including, but not limited to, chicken, turkey, duck, goose, quail, pheasant, parrot, finch, hawk, crow or ratite, for example, ostrich, emu, cassowary. In one useful embodiment, the cell line is derived from a chicken. In one embodiment, the cell line is isolated from a wild type or transgenic avian that expresses the heterologous protein in oviduct cells. In one embodiment, a transgene is introduced into a cell line of the invention wherein the cell line is derived from a wild type avian. In one embodiment, the tumor cell line is contemplated as being derived from certain oviduct tumors, such as an epithelial or mesenchymal tumors, which include, for example, adenocarcinomas, mesenchymal adenomas, leiomyomas, and fibromas. In particularly useful embodiment, the cell line is derived from epithelial adenomas tumors.

The present invention further features a composition comprising the isolated cell lines of the invention within a culture medium. In a related embodiment, the culture medium comprises a heterologous protein expressed by the cell line.

The present invention also features a method of producing a heterologous protein comprising contacting a cell of the invention with a nucleic acid encoding a heterologous protein under conditions suitable for expression of the protein, wherein the cell is sustainable in culture for at least 3, for example, 5, 10 passages, 15 passages, 20 passages, 50 passages or more passages, and then isolating the heterologous protein. The nucleic acid can be transfected into the cell in vitro, for example, by microinjection, electroporation or lipofection or may be transfected into the cell in vivo. The nucleic acid can further include a selectable marker to facilitate selection of cells that express the marker. In an additional related embodiment, the method includes enriching for cells that express the heterologous protein, by, for example, selecting for cells that express gicerin (for example, using a fluorescently labeled antibody that binds gicerin) or selecting for cells that bind neurite outgrowth factor (NOF).

The present invention also features methods of producing a heterologous protein comprising isolating cells that express the protein. In one embodiment, the cell is sustainable in culture for at least 3 or more passages, culturing the cells under conditions suitable for expression of the protein, and then isolating the protein.

The invention also provides heterologous proteins that are produced by the foregoing methods and cell lines. Such proteins can include, for example, antibodies, cytokines, fusion proteins, growth factors, enzymes, structural proteins, interferons, granulocyte-colony stimulating factor, and erythropoietins. Pharmaceutical compositions comprising the heterologous proteins along with a pharmaceutically acceptable carrier also are provided.

Any combination of features described herein is included within the scope of the present invention provided that the features included in any such combination are not mutually inconsistent. Such combinations will be apparent based on this specification and the knowledge of one of ordinary skill in the art.

DETAILED DESCRIPTION

For purposes of describing the invention, the following terms and definitions may be used.

The term "isolated avian oviduct tumor cell" and "avian oviduct tumor cell" or "oviduct tumor cell" as used herein, refers to a cell substantially free of other cell types found in tumors or non-tumorous avian oviduct tissue. An avian oviduct tumor cell line as disclosed herein, may refer to cell lines obtained from one or more cells of avian oviduct tumors or cell lines obtained from one or more cells which have been subjected to in vitro mutagenesis as disclosed herein.

The term "sustainable", as used herein, refers to the ability of the cell or cell line to be passaged in culture for at least three or more, or ten or more times, preferably twenty or more or an infinite number of times.

The term "transfected", as used herein, refers to the uptake of heterologous DNA or RNA by a cell. Transfection, as used herein, encompasses all art-recognized procedures for introducing nucleic acid into cells, including, for example, microinjection, electroporation, chemical transfection and transduction into a cell.

The term "oviduct tumor", as used herein, refers to tumorous tubular gland cells from an avian oviduct (typically the magnum) that secretes egg white proteins including, for example, ovalbumin, ovomucoid, ovoinhibitor, conalbumin, ovomucin and lysozyme. Avian oviduct tumors are typically of an epithelial or mesenchymal nature. Epithelial tumors usually consist of adenomas or adenocarcinomas. Mesenchymal tumors typically consist of adenomas, leiomyomas or fibromas.

As used herein the terms "polypeptide" and "protein" refer to a polymer of amino acids, linked through peptide bonds. The term "polypeptide" includes proteins, protein fragments, protein analogues, oligopeptides and the like. The term polypeptide as used herein can also refer to a peptide.

The term "heterologous protein", as used herein, refers to a protein that is not naturally expressed by the cell that produces the protein.

A "therapeutic protein" or "pharmaceutical protein" is a substance that includes an amino acid sequence (e.g., peptide or protein) which in whole or in part makes up a drug.

The term "avian" as used herein refers to any species, subspecies or race of organism of the taxonomic class ava, such as chicken, turkey, duck, goose, quail, pheasants, parrots, finches, hawks, crows and ratites. The term includes the various known strains of Gallus gallus, or chickens, for example, White Leghorn, Brown Leghorn, Barred-Rock, Sussex, New Hampshire, Rhode Island, Ausstralorp, Minorca, Amrox, California Gray, Italian Partidge-colored, as well as strains of turkeys, pheasants, quails, duck, ostriches and other poultry-commonly bred in commercial quantities.

A "magnum specific" promoter, an "oviduct specific" promoter and a "tubular gland cell (TGC) specific" promoter as used herein, are promoters that are primarily or exclusively active in the tubular gland cells of the avian magnum. Examples of magnum specific or oviduct specific promoters include the ovalbumin promoter, see for example, U.S. patent application Ser. No. 10/733,042, filed Dec. 11, 2003, the ovomucoid promoter, see for example, US patent publication No. US 2005/0176047, published Aug. 11, 2005, and the avian lysozyme promoter, see for example, US patent publication No. US 2003/0140363, published Jul. 24, 2003. The disclosures of each of these three patent applications are incorporated in their entirety herein by reference.

The terms "nucleic acid" and "polynucleotide", as used herein refer to any natural or synthetic array of nucleotides (or nucleosides), for example cDNA, genomic DNA, mRNA, tRNA, oligonucleotides, oligonucleosides and derivatives thereof. The term "gene" as used herein refers to a nucleic acid or polynucleotide (including both RNA or DNA) that encodes genetic information for the synthesis of a whole RNA, a whole protein, or any portion of such whole RNA or whole protein. Genes that are not naturally part of a particular organism's genome are referred to as "foreign genes," "heterologous genes" or "exogenous genes" and genes that are naturally a part of a particular organism's genome are referred to as "endogenous genes". Such genes may be contained in an "expression vector" which, as used herein, refers to a nucleic acid vector that comprises an expression control region operably linked to a nucleotide sequence coding for at least one polypeptide. Such expression vectors therefore drive transcription and expression of the gene.

As used herein, the term "regulatory sequences" includes promoters, enhancers, and other elements that may control gene expression. Standard molecular biology textbooks such as Sambrook et al. eds "Molecular Cloning: A Laboratory Manual" 3rd ed., Cold Spring Harbor Press (2001) may be consulted to design suitable expression vectors that may further include an origin of replication and selectable gene markers. It should be recognized, however, that the choice of a suitable expression vector and the combination of functional elements therein depends upon multiple factors including the choice of the host cell to be transformed and/or the type of protein to be expressed. Representative examples of expression vectors include, for example, bacterial plasmid vectors including expression, cloning, cosmid and transformation vectors such as, but not limited to, pBR322, animal viral vectors such as, but not limited to, modified adenovirus, influenza virus, polio virus, pox virus, retrovirus, and the like and vectors derived from bacteriophage nucleic acid, for example, plasmids and cosmids, artificial chromosomes, such as but not limited to, Yeast Artificial Chromosomes (YACs) and Bacterial Artificial Chromosomes (BACs), and synthetic oligonucleotides like chemically synthesized DNA or RNA. Accordingly, the term "nucleic acid vector" or "vector" as used herein refers to a natural or synthetic single or double stranded plasmid or viral nucleic acid molecule, or any other nucleic acid molecule that can be transfected or transformed into cells and replicate independently of, or within, the host cell genome. A nucleic acid can be inserted into a vector by cutting the vector with restriction enzymes and ligating the pieces together. The nucleic acid molecule can be RNA or DNA.

The term "heterologous polypeptide", as used herein, refers to a polypeptide that does not naturally occur in a host cell.

The term "expressed" or "expression" as used herein refers to the transcription of a nucleotide sequence into an RNA nucleic acid molecule at least complementary in part to a region of one of the two nucleic acid strands of a gene coding sequence and/or to the translation from an RNA nucleic acid molecule into a protein or polypeptide.

The term "operably linked" as used herein refers to the configuration of coding and control sequences, for example, within an expression vector, so as to achieve transcription and/or expression of the coding sequence. Thus, control sequences operably linked to a coding sequence are capable of effecting the expression of the coding sequence and regulating in which tissues, at what developmental time points, or in response to which signals, and the like, a gene is expressed. A coding sequence is operably linked to or under the control of transcriptional regulatory regions in a cell when DNA polymerase will bind the promoter sequence and transcribe the coding sequence into mRNA that can be translated into the encoded protein. The control sequences need not be contiguous with the coding sequence, so long as they function to direct the expression thereof. Thus, for example, intervening untranslated or transcribed sequences can be present between a promoter sequence and the coding sequence and the promoter sequence can still be considered "operably linked" to the coding sequence. Such intervening sequences include but are not limited to enhancer sequences which are not transcribed or are not bound by polymerase.

The terms "gene expression control regions" or "gene expression controlling regions" as used herein refer to nucleotide sequences that are associated with a nucleic acid sequence and which regulate, in whole or in part, the expression of the nucleic acid sequence, for example, regulate in whole or in part the transcription of a nucleotide sequence.

The term "stable cell line" refers to a cell or cell line that can be passaged 20 or more times, for example, an immortal cell line is a stable cell line.

The term "transient cell line" refers to a cell or cell line that is not immortal. For example, a cell line that cannot be passaged more than 20 times is a transient cell line.

The terms "transformation" and "transfection" as used herein refer to the process of inserting a nucleic acid into a host cell. Many techniques are well known to those skilled in the art to facilitate transformation or transfection of a nucleic acid into a prokaryotic or eukaryotic cell. These methods include a variety of techniques, which may include, but are not limited to, viral transduction, microinjection, treating the cells with high concentrations of salt such as, but not only, a calcium or magnesium salt, an electric field, detergent, or liposome mediated transfection, to render the host cell competent for the uptake of the nucleic acid molecules, and by such methods as sperm-mediated and restriction-mediated integration. Other transfecting agents include but are not limited to lipofectin, lipfectamine, DIMRIE C and Effectin (Qiagen), unifectin, maxifectin, DOTMA, DOGS (Transfectam; dioctadecylamidoglycylspermine), DOPE (1,2-dioleoyl-sn-glycero-3-phosphoethanolamine), DOTAP (1,2-dioleoyl-3-trimethylammonium propane), DDAB (dimethyl dioctadecytammonium bromide), DHDEAB (N,N-di-n-hexadecyl-N,N-dihydroxyethyl ammonium bromide), HDEAB (N-n-hexadecylN,N-dihydroxyethylammonium bromide), polybrene, or poly(ethylenimine) (PEI). These non-viral agents have the advantage that they can facilitate stable integration of xenogeneic DNA sequences into the vertebrate genome, without size restrictions commonly associated with virus-derived transfecting agents. Certain methods useful for the introduction of nucleic acid into a cell are disclosed in, for example, U.S. patent application Ser. No. 11/159,973, filed Jun. 23, 2005 and U.S. patent application Ser. No. 10/811,136, filed Mar. 26, 2004. The disclosures of each of these two patent applications are incorporated in their entirety herein by reference.

The term "enriched", as used herein with respect to avian oviduct specific cells, refers to an increase in the number of such cells relative to the total cell population in which they are contained (i.e., an increase in the number of oviduct cells relative to the number of non-oviduct cells).

As used herein, a "transgenic avian" includes an avian, for example, a chicken, turkey, duck, goose, quail, pheasant, parrot, finch, hawk, crow or ratite, for example, ostrich, emu, cassowary, in which one or more, for example, essentially all of the cells of the avian include a transgene. The transgene is introduced into the cell, directly or indirectly by introduction into a precursor of the cell, for example, by microinjection, transfection or infection, for example, by infection with a recombinant virus. The term genetic manipulation includes the introduction of a recombinant DNA molecule. This molecule may be integrated within a chromosome, or it may be extrachromosomally replicating DNA.

The terms "recombinant nucleic acid" and "recombinant DNA" as used herein refer to a combination of at least two nucleic acids that is not naturally found in a eukaryotic or prokaryotic cell in that particular configuration. The nucleic acids may include, but are not limited to, nucleic acid vectors, gene expression regulatory elements, origins of replication, suitable gene sequences that when expressed confer antibiotic resistance, protein-encoding sequences and the like. The term "recombinant polypeptide" is meant to include a polypeptide produced by recombinant DNA techniques such that it is distinct from a naturally occurring polypeptide either in its location, purity or structure. Generally, such a recombinant polypeptide will be present in a cell in an amount different from that normally observed in nature.

As used herein, the term "transgenic cell" refers to a cell containing a transgene.

As used herein, the term "marker sequence" refers to a nucleic acid molecule that is used to identify those cells that have incorporated the targeting construct into their genome. For example, the marker sequence can be a sequence encoding a protein which confers a detectable trait on the cell, such as an antibiotic resistance gene, for example, neomycin resistance gene, or an assayable enzyme not typically found in the cell, for example, alkaline phosphatase, horseradish peroxidase, luciferase, beta-galactosidase and the like.

As used herein, a "naturally-occurring" nucleic acid molecule refers to an RNA or DNA molecule having a nucleotide sequence that occurs in an organism found in nature.

As used herein, the term "host cell" is intended to refer to a cell into which a nucleic acid molecule of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. A host cell may be a mammalian cell, for example, a human cell. In certain embodiments, the host cell is an epithelial cell, for example, a pancreatic epithelial cell.

As used herein, the term "transgene" means a nucleic acid sequence (encoding, for example, a human interferon polypeptide) that is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (for example, it is inserted at a location that differs from that of the natural gene or its insertion results in a knockout). A transgene also includes a regulatory sequence designed to be inserted into the genome such that it regulates the expression of an endogenous coding sequence, for example, to increase expression and/or to change the timing and or tissue specificity of expression, for example, to effect "gene activation".

The term "antibody" as used herein refers to polyclonal and monoclonal antibodies and fragments thereof, and immunologic binding equivalents thereof. The term "antibody" refers to a homogeneous molecular entity, or a mixture such as a polyclonal serum product made up of a plurality of different molecular entities, and broadly encompasses naturally-occurring forms of antibodies (for example, IgG, IgA, IgM, IgE) and recombinant antibodies such as single-chain antibodies, chimeric and humanized antibodies and multispecific antibodies. The term "antibody" also refers to fragments and derivatives of all of the foregoing, and may further comprise any modified or derivatised variants thereof that retains the ability to specifically bind an epitope. Antibody derivatives may comprise a protein or chemical moiety conjugated to an antibody. A monoclonal antibody is capable of selectively binding to a target antigen or epitope. Antibodies may include, but are not limited to polyclonal antibodies, monoclonal antibodies (mAbs), humanized or chimeric antibodies, camelized antibodies, single chain antibodies (scFvs), Fab fragments, $F(ab')_2$ fragments, disulfide-linked Fvs (sdFv) fragments, for example, as produced by a Fab expression library, anti-idiotypic (anti-Id) antibodies, intrabodies, synthetic antibodies, and epitope-binding fragments.

The techniques used to isolate and characterize nucleic acids and proteins according to the methods of the present invention are well known to those of skill in the art and standard molecular biology and biochemical manuals may be consulted to select suitable protocols without undue experimentation. See, for example, Sambrook et al. (2001) Molecular Cloning: A Laboratory Manual, 3rd ed., Cold Spring Harbor Press, the content of which is herein incorporated by reference in its entirety.

Some abbreviations used in the present specification include the following: aa, amino acid(s); bp, base pair(s); cDNA, DNA complementary to RNA; min, miunte(s); nt, nucleotide(s); SSC, sodium chloride-sodium citrate; UTR, untranslated region; DMSO, dimethyl sulfoxide; ul, microliter; and uM; micromolar.

Various aspects of the invention are described in further detail in the following.

One particularly useful aspect of the present invention relates to hybrid cell lines which can be used for, among other things, promoter assays and/or heterologous protein expression. Such assays can be useful to detect or to quantify the activity of gene expression controlling elements such as promoters which are active in tubular gland cells, including without limitation, tubular gland cell (TGC)-specific promoters. For example, the cells can be useful to detect or quantify the activity of certain promoters such as promoters for egg-white proteins, including ovalbumin, ovomucoid, conalbumin, ovomucin and lysozyme. In one useful embodiment, cell lines of the invention are used to produce useful proteins in useful quantity in cell culture.

Another particularly useful embodiment of the invention relates to stable cell lines and their use. In one embodiment to produce cell lines of the invention, one or more cells of an immortalized cell line such as a mammalian cell line, for example, and without limitation, a mouse myeloma cell(s) containing a TGC-specific promoter controlling expression of a selectable marker (for example, and without limitation, puromycin or neomycin, GFP) can be fused with one or more TGCs (e.g., primary tubular gland cells) isolated from an avian oviduct (e.g., a chicken oviduct) to produce a hybrid cell. In one embodiment, the TGCs are isolated from the oviduct of a mature avian. TGCs can be isolated by any useful method, for example, as disclosed elsewhere herein. Any useful method may be employed to produce the cell fusions. For example, and without limitation, well known cell fusion methods such as polyethylene glycol cell fusions may be employed. In other embodiments, the TGC-specific promoter controlling expression of a selectable marker is introduced into the TGC before fusion to the immortal cell or is introduced into the hybrid cell after fusion.

Nucleic acid containing the TGC-specific promoter which controls expression of the selectable marker may be introduced into the cells by any useful method. For example, and without limitation, the nucleic acid can be introduced into the cells by transfection, electroporation and lipofection using standard methodologies well known in the art. The nucleic acid may be contained in any useful construct including, but not limited to, episomal constructs or useful vectors such as plasmids, phagmids, viral vectors and artificial chromosome (e.g., BAC, YAC, HAC, MAC and the like); For example, artificial chromosomes such as those disclosed in U.S. patent application Ser. No. 11/362,064, filed Feb. 24, 2006, the disclosure of which is incorporated in its entirety herein by reference, may be employed in the present invention. The nucleic acid may also be integrated into the cell genome.

The nucleic acid containing the promoter to be tested, or any other nucleic acid to be introduced into cells in accordance with the invention, may be introduced into the cells by any useful method. For example, and without limitation, the nucleic acid can be introduced into the cells by transfection, electroporation and lipofection using standard methodologies well known in the art. The nucleic acid may be contained in any useful construct including, but not limited to, episomal constructs or useful vectors such as plasmids, phagmids, viral vectors, artificial chromosomes (e.g., BAC, YAC, HAC, MAC and the like). For example, artificial chromosomes such as those disclosed in U.S. patent application Ser. No. 11/362,064, filed Feb. 24, 2006, the disclosure of which is incorporated in its entirety herein by reference, may be employed in the present invention. The nucleic acid may also be integrated into the cell genome.

Without wishing to limit the invention to any particular theory or mechanism of operation, it is believed that in one embodiment of the invention, TGC transcription factors contained in the hybrid cell lines of the invention are effective to facilitate transcription of a coding sequence for a selectable marker which is under the control of an oviduct specific promoter in the hybrid cell. Therefore, one aspect of the invention relates to non-TGC cells which contain TGC transcription factors and/or TGC transcription factor encoding nucleic acids. In addition, it is believed that the TGC transcription factors can facilitate transcription of a coding sequence which is under the control of the oviduct specific promoter providing substrate for an oviduct specific promoter assay.

Any suitable assay may be used to determine the activity of the promoter being tested. That is, the TGC-specific promoter may be operably linked to a coding sequence which encodes any product that can be assayed for in a useful assay. Assays that may be used include those based on, for example, luciferase, GFP or β-galactosidase. In one embodiment, an ELISA assay is employed. For example, the cell lines can be transfected with expression constructs containing TGC-specific promoters controlling expression of various pharmaceutical proteins (i.e. monoclonal antibodies, EPO, GCSF) which can be assayed for by ELISA. Such cell lines can also be useful for the production of commercially useful amounts of such proteins.

In one embodiment, cells produced as disclosed herein can be employed in transient cell line fusion assays. Such assays are also useful to detect or quantify tubular gland cell-specific gene expression.

To produce transient cell lines of the invention, one or more cells of an immortalized cell line such as a mammalian cell line, for example, and without limitation, a Chinese hamster ovary (CHO) cell(s) is fused with one or more tubular gland cells (TGCs) (e.g., primary tubular gland cells) isolated from an avian oviduct (e.g., a chicken oviduct). In one embodiment, the TGCs are isolated from the oviduct of a mature avian. Any useful method may be employed to produce the cell fusions. For example, and without limitation, well known cell fusion methods such as polyethylene glycol cell fusions may be employed.

In one embodiment, the promoter to be studied is contained in an expression construct operably linked to a coding sequence, the expression of which may be assayed for. The expression construct may be similar to such expression constructs disclosed herein for use with stable cell line assays. The expression construct may be initially inserted (i.e., transformed) into an immortal cell used in the fusion and/or in an oviduct cell used in the fusion. In one embodiment, the expression construct is inserted (i.e., transformed) into a hybrid cell produced by the fusion. Assays are performed essentially as performed for the stable cell lines.

The present invention also relates to the isolation and enrichment of avian oviduct cells to obtain sustainable cell lines that can be passaged multiple times in cell culture and can be used for long-term production of heterologous polypeptides at higher yields. The methods of the present invention involve the manipulation and/or propagation of oviduct cells derived from either wild-type or transgenic avians. The cells may be isolated directly from the wild-type or transgenic avians or may be obtained by genetically altering (for example, by mutagenesis) cells taken from oviduct tissue of wild-type or transgenic avians. Preferably, the transgenic avians produce heterologous protein in oviduct cells.

Cell lines of the present invention may be obtained using any useful method. In one embodiment, tumor cell lines are derived or obtained from avians having tumors in their reproductive organs, in particular, the oviduct, for example, the infundibulum, magnum (e.g., TGCs), isthmus, uterus, vagina, cloaca and vent. Tumors obtained from other organs and tissue of avians such as chickens are also contemplated for use in accordance with the invention, because, for example, certain non-oviduct tumors may be useful for expressing transcription factors and/or other regulatory elements responsible for expression of oviduct specific proteins such as ovalbumin, ovomucoid, ovomucin, ovotransferrin and avian lysozyme proteins even though the tumor is not derived from oviduct tissue. Such cell lines are contemplated for use in the present invention for producing heterologous proteins, the coding sequence of which is under the control of an oviduct specific promoter. For example, the invention contemplates the use of cells and cell lines obtained from tumors of the liver, stomach, lungs, gizzard, intestine, colon, skin, blood cells, bone marrow, kidneys, spleen, heart, brain, pancreas, testis, and muscle tissue of avians which are capable of expressing proteins that typically are made primarily or exclusively in TGCs.

It has been determined that avians, such as chickens, can spontaneously produce tumors in the oviduct or other tissue and that such tumors become more prevalent as the avian ages. For example, it is believed that more than half of the domestic chickens over the age of five years have such tumors. In addition, the tumors can be induced in avians using mutagens or carcinogens as is understood in the field of mutation research. In one particularly useful embodiment, the avian tumors arise from one or more tubular gland cells.

Examples of carcinogens and mutagens contemplated for use in producing avian oviduct tumors include, without limitation, acrylonitrile, adriamycin, aflatoxins, arsenic and arsenic compounds, asbestos, benzene, benzidine n,n-bis(2-chloroethyl)-2-naphthylamine, benzo (a) pyrene, beryllium and beryllium compounds, bis(chloromethyl)ether, 1,4-butanediol, cadmium and cadmium compounds, carbon tetrachloride, chloroform, chromium and chromium compounds, chloromethyl methyl ether, conjugated estrogens, 2,4-diaminotoluene, 1,2-dibromo-3-chloropropane, dichloroethane, ddt, diethylstilbestrol, diethylsulfate, 1,4-dioxane, ethylene dibromide (edb), ethylene oxide, ethylene thiourea, ethyl methanesulfonate, formaldehyde (formalin solutions), hydrazine and hydrazine sulfate, lead acetate and lead phosphate, 3-methylcholanthrene, methylhydrazine, methyl iodide, methylene chloride, methyl methanesulfonate, 1-methyl-3-nitro-1-nitrosoguanidine, 4,4-methylenebis(2-chloroaniline) (mboca), 2-napthylamine, nickel and nickel compounds, 4-nitrobiphenyl, nitrogen mustard, 2-nitropropane, n-nitrosodi-n-bytylamine, n-nitrosodiethyl-amine, n-nitrosodimethyl-amine, n-nitroso-n-ethylurethane, oxymetholone, phenacetin, phenyloin, polychlorinated byphenyls, procarbazine, progesterone, 1,3-propane sultone, b-propiolactone, reserpine, saccharin, safrole, selenium sulfide, 2,3,7,8-tetrachlorodibenzo-p-dioxin (tcdd), thioacetaminde, thiourea, thoriumdioxide, o-toluidine, m-troluenediamine, toxaphene, tris (1 aziridinyl)phosphine sulfide, tris(2,3-dibromopropyl) phosphate, uracil mustard, urethane and vinyl chloride.

In another embodiment, avian oviduct cells, for example, tubular gland cells, may be immortalized in vitro. Immortalization of the avian cells may be spontaneous, or may be induced by mutagens or by transfection using certain oncogenes. Mutagens, such as those disclosed for use herein for the production of avian tumors, can be employed for the in vitro production of immortal avian oviduct tumor cell lines utilizing methodologies well known to those of ordinary skill in the art. Examples of oncogenes which may be useful for the production of immortalized cells include, without limitation, genes for: growth factors, growth factor receptors, protein kinases, signal transducers, nuclear phosphoproteins, and transcription factors. Such oncogenes may be employed by a person of ordinary skill in the field utilizing methods known in the art to produce immortal avian oviduct tumor cell lines.

Oviduct tumor cells can be isolated from tumorous avian oviducts using any suitable tissue isolation technique known in the art. For example, tumor cells can be obtained by removing and dissecting the oviduct of a female avian to expose the luminal side. The oviduct is examined and any tumors, polyps or abnormal growths are excised for processing. Avian oviduct tumors are typically of an epithelial or mesenchymal nature. Epithelial tumors usually consist of adenomas or adenocarcinomas. Mesenchymal tumors typically consist of adenomas, leiomyomas or fibromas. Once collected, the tumor can be placed in a suitable basal salt medium, such as F12, and stored on ice for up to 4 hours.

The oviduct tissue or certain other avian tissues employed in the invention can be finely minced, for example, into 1-2 mm pieces, and incubated in a suitable media, such as F12 with collagenase (for example, 0.08-8.0 mg/ml) and dispase (for example, 0.1-10.0 mg/ml). In one embodiment, the tissue is shaken at 37-42° C. for 1 to 30 minutes, (400 rpm) and triturated to generate clumps each consisting of 100-1000 cells. Clumps of cells are allowed to settle out and the supernatant, containing red blood cells and cellular debris, is discarded. The clumps are suspended in pre-warmed F12 media, supplemented with collagenase (0.08-8.0 mg/ml) and dispase (0.1-10.0 mg/ml), and incubated at 37-42° C. with shaking (400 rpm). Clumps are triturated every ten minutes to generate clumps consisting of 5-100 cells that are subsequently pelleted with low speed centrifugation (~800 rpm). The resultant pellet is suspended in ice cold F12 and filtered through a single layer of surgical gauze tape to remove larger clumps. Cells are washed twice with ice cold F12, pelleted and suspended in the growth medium at an $OD_{600}$ of 0.3-3.0. Cells such as TGCs can be collected with this technique and are suitable for use in the methods described herein.

Culturing of cells, for example, cells obtained from the avian tissue, can use a basal salt media, such as F12, DMEM, MEM, and the like. supplemented with fetal calf serum, fetal bovine serum, new born calf serum, goat serum or chicken serum to 0.1%-15% total volume, 0.01-1000 nM estrogen, 1-10000 nM corticosterone and 0.01-1000 uM insulin. This medium is hereafter referred to as "growth media". Cells derived from oviduct tumors can be isolated through multiple passages in such appropriate growth media. Initially, cells isolated from the original oviduct samples are grown in growth media (for example, at 1-5% $CO_2$ and 37°-42° C.)

until the culture reaches confluency or the diameter of cell clumps reaches approximately one millimeter. Cell clumps and monolayers are subsequently treated with basal salts media containing collagenase (0:08-8 mg/ml) and dispase (0.1-10 mg/ml) to produce single cell suspension. Cells are pelleted and washed twice with basal salt media. After final wash, the cell pellet is suspended in growth media at a cell density of $1 \times 10^4$-$1 \times 10^6$ cells per milliliter.

Single colony isolates of cultured cells can be isolated using limiting dilution techniques. For example, cultured cells are dispersed as described. Single cells are plated in each well of 96 well plate and incubated in growth media. Alternatively single cells can be cultured on a monolayer of cells such as whole embryo fibroblasts, STO (Martin and Evans, Proc Natl Acad Sci USA, 1975. 72: 1441-5), or LMH (Kawaguchi et al., Cancer Res, 1987. 47: 4460-4). Supernatant from each well can be collected every three days and the levels of ovalbumin, ovomucoid and lysozyme determined by ELISA (ovomucoid and ovalbumin) or bioactivity assay (lysozyme). Clones that express any or all of the defined egg white proteins are passaged as needed to maintain viability.

Avian cells isolated or produced as described herein can be transfected with nucleic acids, for example, transgenes, encoding a variety of heterologous proteins using techniques well known in the art, such that sustained production of the proteins is achieved. Typically, the nucleic acid is present within a suitable expression vector. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced, for example, bacterial vectors having a bacterial origin of replication and episomal mammalian vectors. Other vectors, such as non-episomal mammalian vectors, are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include other forms of expression vectors, such as viral vectors, for example, replication defective retroviruses, adenoviruses and adeno-associated viruses.

Suitable vectors for use in the present invention comprise nucleic acid sequence encoding heterologous protein(s), that are operatively linked to one or more regulatory sequences, for example, promoter sequences. The phrase "operably linked" is intended to mean that the nucleotide sequence of interest, for example, the sequence encoding the heterologous protein, is linked to the regulatory sequence(s) in a manner which allows for expression of the nucleotide sequence (for example, in an in vitro transcription/translation system or in a host cell when the vector is introduced into the host cell). The term "regulatory sequence" is intended to include promoters, enhancers and other expression control elements, for example, polyadenylation signals. Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells, for example, oviduct specific regulatory sequences. Other elements included in the design of a particular expression vector can depend on such factors as the choice of the host cell to be transformed, the level of expression of protein desired and the like. The expression vectors of the invention can be introduced into host cells to thereby produce proteins or peptides, including fusion proteins or peptides, encoded by nucleic acids as described herein.

Vectors as described herein can be introduced into isolated or produced as disclosed herein using any of a variety of well known techniques well known in the field. Suitable methods may be described, for example, in Sambrook et al., Molecular Cloning: A Laboratory Manual, Cold Spring Harbor Laboratory, New York (1992), which is hereby incorporated by reference. See, also, Ausubel et al., Current Protocols in Molecular Biology, John Wiley and Sons, Baltimore, Md. (1989); Hitt et al., "Construction and propagation of human adenovirus vectors," in Cell Biology: A Laboratory Handbook, Ed. J. E. Celis., Academic Press. 2.sup.nd Edition, Volume 1, pp: 500-512, 1998; Hitt et al., "Techniques for human adenovirus vector construction and characterization," in Methods in Molecular Genetics, Ed. K. W. Adolph, Academic Press, Orlando, Fla., Volume 7B, pp: 12-30, 1995; Hitt, et al., "Construction and propagation of human adenovirus vectors," in Cell Biology: A Laboratory Handbook, Ed. J. E. Celis. Academic Press. pp: 479-490, 1994, each of which is also hereby incorporated by reference. The methods include, for example, stable or transient transfection, lipofection, electroporation and infection with recombinant viral vectors.

Cell lines of the invention transfected or transformed as described herein are also referred to herein as "recombinant host cells". The term "recombinant host cell" refers not only to the initial cell transfected, but also to the progeny or potential progeny of the cell. Because certain modifications may occur in succeeding generations due to either mutation or environmental influences, such progeny may not, in fact, be identical to the parent cell, but are still included within the scope of the term as used herein.

Selection vectors that contain, for example, oviduct specific promoters, such as ovalbumin, ovomucoid or lysozyme promoters or other suitable non-specific promoters that drive expression of an antibiotic resistance gene such as neomycin, hygromycin or puromycin, can be transfected into avian tumor cells using the art-recognized techniques such as those described herein. Presence of the selection vector in the cell can be transient or clones that contain integrated copies of the selection vector can be selected for.

In one embodiment, the presence of the appropriate antibiotic, cells will survive if they are able to initiate transcription from the oviduct specific promoter located on the selection vector provided. This technique therefore selects for those cells with active oviduct specific promoters. In one useful embodiment, cells will survive if they are able to initiate transcription of an antibiotic resistance gene from the oviduct specific promoter located on a selection vector. This technique therefore selects for those cells with active cloned oviduct specific promoters. In one aspect of the invention, an oviduct specific promoter drives transcription of an RNA molecule encoding both an antibiotic resistance protein product and a protein of interest such as a pharmaceutical composition. In such a case, an internal ribosome entry site may be employed between the two coding sequences.

The foregoing selection methods can be used with the initial primary cell culture or cells from subsequent passages.

In one embodiment, the selection vectors described herein drive expression of a fluorescent protein, such as Enhanced Green Fluorescence Protein (EGFP). Cells that transcribe the EGFP can then be sorted and collected using standard Florescence Assisted Cell Sorting (FACS) techniques. Cells collected in this manner can be cultured and additional rounds of selection used to isolate cells with the desired egg white producing phenotype.

Metastasis of epithelial tumors often involves cell adhesion molecules (CAMs) and epithelial-extracellular matrix (ECM) proteins (Takeichi, Curr Opin Cell Biol, 1993. 5: 806-11; Evans, Cell Biol Int Rep, 1992. 16: 1-10). Tsukamoto demonstrated that oviductal tumor cells bind to neurite outgrowth factor (NOF) through interactions with gicerin, a CAM expressed by cells of oviduct tumors. This interaction is evidenced by the fact that oviductal tumor cells pre-incubated with an anti-gicerin antibody exhibited decreased binding to purified and cell associated NOF. While NOF is expressed by mesentery cells of oviduct tumors, it is also expressed on chicken gizzard, skeletal muscle, heart, liver and ciliary ganglion cells (Hayashi and Miki, J Biol Chem, 1985. 260: 14269-78).

The ability of certain cells of the invention cells to bind NOF can be used as a tool to isolate and enrich for metastatic cells of avian oviduct tumors. Tumor cells can be collected as described earlier and placed on tissue culture plates coated with purified NOF or on a monolayer culture of avian cells prepared from the gizzard, skeletal muscle, heart, liver or ciliary ganglion, or mesenchym of an oviductal tumor. This can be done, for example, by incubating the cells for approx. 1 hour at 37°-41° C. at 5% $CO_2$ to allow attachment of gicerin positive cells to the purified or cell associated NOF. The cultures are washed twice with warm (37°-41° C.) DMEM to dislodge any unbound cells. Seeded cells are allowed to grow until colonies consisting of 10-1000 cells form. Colonies that arise from these cells are removed by placing a cloning cylinder around the colony and removing the culture media. The colony is then digested and liberated from the underlying NOF coated plate or NOF expressing cell monolayer using F12 containing collagenase (0.08-8 mg/ml) and dispase (0.1-10 mg/ml). The colony and its' cells are placed in an Ependorff tube and further digested with fresh F12 collagenase/dispase media. Once digestion is completed the cells are placed back into culture. This process can be repeated with the isolated colonies additional times to enrich for the cells. After several rounds of enrichment the cultures can be digested and single colonies from these cultures screened for production of ovalbumin, ovomucoid or lysozyme and viability after multiple passages.

In one embodiment, cells of the invention that express gicerin are isolated using an anti-gicerin antibody and FACS. Cells are initially incubated with an anti-gicerin antibody. Cells are then washed to remove unbound antibody and then incubated with a detection antibody specific for the isotype of the anti-gicerin antibody. After removing unbound detection antibody, the cells that stain positive are sorted and collected using standard FACS techniques. Cells collected in this manner can be cultured and additional rounds of selection used to isolate cells with the desired heterologous protein producing phenotype. Cells and their subsequent lines should remain viable for multiple passages in a defined growth medium. The growth medium can contain, for example, supplements of fetal calf serum, fetal bovine serum or chicken serum to 0.1%-15% total volume, and 0.01-1000 nM estrogen, 1-10000 nM corticosterone and 0.01-1000 uM insulin.

Cell lines of the invention can be assessed for the ability to express heterologous proteins using a variety of art-recognized techniques. Non-limiting examples of such methods include immunological methods for detection of secreted, cell-surface, cytoplasmic, or nuclear polypeptides, protein purification methods, protein function or activity assays, nucleic acid hybridization methods, nucleic acid reverse transcription methods, and nucleic acid amplification methods. The expressed protein can be detected, for example, by ELISA or bioactivity assay. Such heterologous proteins can be any expressible protein and may include, for example, therapeutic proteins such as cytokines, growth factors, enzymes, structural proteins, immunoglobulins, granulocyte-colony stimulating factor, or any other polypeptide of interest that is capable of being expressed by an avian cell or tissue. In one embodiment, the heterologous protein is mammalian, for example, a human protein or the heterologous protein may comprise a portion of a mammalian or human protein (e.g., a fusion protein).

In one embodiment, expression of the protein is assessed using an antibody, for example a radio-labeled, chromophore-labeled, fluorophore-labeled, or enzyme-labeled antibody, an antibody derivative, such as an antibody conjugated with a substrate or with the protein or ligand of a protein-ligand pair, for example biotin-streptavidin, or an antibody fragment, for example a single-chain antibody, an isolated antibody hypervariable domain, which binds specifically with a polypeptide or fragment thereof, including a polypeptide which has undergone all or a portion of its normal post-translational modification.

In another embodiment, expression of the protein is assessed by preparing mRNA/cDNA (i.e. a transcribed polynucleotide) from cells, and by hybridizing the mRNA/cDNA with a reference polynucleotide which is a complement of a polypeptide nucleic acid, or a fragment thereof. cDNA can, optionally, be amplified using any of a variety of polymerase chain reaction methods prior to hybridization with the reference polynucleotide. Expression of one or more proteins can likewise be detected using quantitative PCR to assess the level of expression of the protein(s).

The invention also contemplates the purification of proteins produced in accordance with the invention by useful methods apparent to one skilled in the art.

The invention provides methods for producing multimeric proteins, for example, immunoglobulins, such as antibodies, and antigen binding fragments thereof.

In one embodiment of the present invention, the multimeric protein is an immunoglobulin, wherein the first and second heterologous polypeptides are an immunoglobulin heavy and light chains respectively. Illustrative examples of this and other aspects and embodiments of the present invention for the production of heterologous multimeric polypeptides in avian cells are fully disclosed in U.S. patent application Ser. No. 09/877,374, filed Jun. 8, 2001, published as US-2002-0108132-A1 on Aug. 8, 2002, and U.S. patent application Ser. No. 10/251,364, filed Sep. 18, 2002, each of which are incorporated herein by reference in their entirety. In one embodiment of the present invention, therefore, the multimeric protein is an immunoglobulin wherein the first and second heterologous polypeptides are an immunoglobulin heavy and light chain respectively.

In the various embodiments of this aspect of the present invention, an immunoglobulin polypeptide encoded by the transcriptional unit of at least one expression vector may be an immunoglobulin heavy chain polypeptide comprising a variable region or a variant thereof, and may further comprise a D region, a J region, a C region, or a combination thereof. An immunoglobulin polypeptide encoded by the transcriptional unit of an expression vector may also be an immunoglobulin light chain polypeptide comprising a variable region or a variant thereof, and may further comprise a J region and a C region. It is also contemplated to be within the scope of the present invention for the immunoglobulin regions to be derived from the same animal species, or a mixture of species including, but not only, human, mouse, rat, rabbit and chicken. In certain embodiments, the antibodies are human or humanized.

In other embodiments of the present invention, the immunoglobulin polypeptide encoded by the transcriptional unit of at least one expression vector comprises an immunoglobulin heavy chain variable region, an immunoglobulin light chain variable region, and a linker peptide thereby forming a single-chain antibody capable of selectively binding an antigen.

Another aspect of the present invention provides a method for the production of heterologous protein capable of forming an antibody suitable for selectively binding an antigen including producing a cell line incorporating at least one transgene, wherein the transgene encodes at least one heterologous polypeptide selected from an immunoglobulin heavy chain variable region, an immunoglobulin heavy chain comprising a variable region and a constant region, an immunoglobulin light chain variable region, an immunoglobulin light chain comprising a variable region and a constant region, and a single-chain antibody comprising two peptide-linked immunoglobulin variable regions.

In one embodiment of the invention, the isolated heterologous protein is an antibody capable of selectively binding to an antigen. In one embodiment, the antibody may be generated by combining at least one immunoglobulin heavy chain variable region and at least one immunoglobulin light chain variable region, for example, cross-linked by at least one disulfide bridge. The combination of the two variable regions will generate a binding site capable of binding an antigen using methods for antibody reconstitution that are well known in the art.

The present invention is useful for the production of many biological products such as, pharmaceutical compositions. For example, the present invention can be useful for the production of biological molecules such as hormones including cytokines (i.e., secreted polypeptides that affect a function of cells and modulates an interaction between cells in an immune, inflammatory or hematopoietic response), antibodies and other useful pharmaceutical molecules which include polypeptides. Cytokines include, but are not limited to, monokines and lymphokines. Examples of cytokines include, but are not limited to, interferon α2b, Interleukin-1 (IL-1), Interleukin-6 (IL-6), Interleukin-8 (IL-8), Tumor Necrosis Factor-α (TNF-α) and Tumor Necrosis Factor β (TNF-β), antibodies such as polyclonal and monoclonal antibodies and fragments thereof, and immunologic binding equivalents thereof. Antibodies may include, but are not limited to polyclonal antibodies, monoclonal antibodies (MAbs), humanized or chimeric antibodies, single chain antibodies, FAb fragments, F(Ab')$_2$ fragments, fragments produced by a FAb expression library, anti-idiotypic (anti-Id) antibodies, and epitope-binding fragments thereof. Also contemplated is the production of antibody fusion proteins, for example, Fc fusion proteins in accordance with the present methods. The methods of the present invention can also be useful for producing immunoglobulin polypeptides which are constituent polypeptides of an antibody or a polypeptide derived therefrom. An "immunological polypeptide" may be, but is not limited to, an immunological heavy or light chain and may include a variable region, a diversity region, joining region and a constant region or any combination, variant or truncated form thereof. Immunological polypeptides also include single-chain antibodies comprised of, but not limited to, an immunoglobulin heavy chain variable region, an immunoglobulin light chain variable region and optionally a peptide linker.

Other specific examples of therapeutic proteins which are contemplated for production as disclosed herein include, without limitation, factor VIII, b-domain deleted factor VIII, factor VIIa, factor IX, anticoagulants; hirudin, alteplase, tpa, reteplase, tpa, tpa—3 of 5 domains deleted, insulin, insulin lispro, insulin aspart, insulin glargine, long-acting insulin analogs, hgh, glucagons, tsh, follitropin-beta, fsh, gm-csf, pdgh, ifn alpa2a, inf-apha, inf-beta 1b, ifn-beta 1a, ifn-gammalb, il-2, il-11, hbsag, ospa, murine mab directed against t-lymphocyte antigen, murine mab directed against tag-72, tumor-associated glycoprotein, fab fragments derived from chimeric mab, directed against platelet surface receptor gpII(b)/III(a), murine mab fragment directed against tumor-associated antigen ca125, murine mab fragment directed against human carcinoembryonic antigen, cea, murine mab fragment directed against human cardiac myosin, murine mab fragment directed against tumor surface antigen psma, murine mab fragments (fab/fab2 mix) directed against hmw-maa, murine mab fragment (fab) directed against carcinoma-associated antigen, mab fragments (fab) directed against nca 90, a surface granulocyte nonspecific cross reacting antigen, chimeric mab directed against cd20 antigen found on surface of b lymphocytes, humanized mab directed against the alpha chain of the il2 receptor, chimeric mab directed against the alpha chain of the il2 receptor, chimeric mab directed against tnf-alpha, humanized mab directed against an epitope on the surface of respiratory synctial virus, humanized mab directed against her 2, i.e., human epidermal growth factor receptor 2, human mab directed against cytokeratin tumor-associated antigen anti-ctla4, chimeric mab directed against cd 20 surface antigen of b lymphocytes domase-alpha DNAse, beta glucocerebrosidase, tnf-alpha, il-2-diptheria toxin fusion protein, tnfr-lgg fragment fusion protein laronidase, dnaases, alefacept, darbepoetin alfa (colony stimulating factor), tositumomab, murine mab, alemtuzumab, rasburicase, agalsidase beta, teriparatide, parathyroid hormone derivatives, adalimumab (Igg1), anakinra, biological modifier, nesiritide, human b-type natriuretic peptide (hbnp), colony stimulating factors, pegvisomant, human growth hormone receptor antagonist, recombinant activated protein c, omalizumab, immunoglobulin e (Ige) blocker and Ibritumomab tiuxetan.

Examples of certain antibodies that can be produced in methods of the invention may include but are not limited to HERCEPTIN® (Trastuzumab) (Genentech, CA) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); ICM3 which is a humanized anti-ICAM3 antibody (ICOS Pharm); IDEC-114 which is a primatied anti-CD80 antibody (IDEC Pharm/Mitsubishi); ZEVALIN™ which is a radiolabelled murine anti-CD20 antibody (IDEC/Schering AG); IDEC-131 which is a humanized anti-CD40L antibody (IDEC/Eisai); IDEC-151 which is a primatized anti-CD4 antibody (IDEC); IDEC-152 which is a primatized anti-CD23 antibody (IDEC/Seikagaku); SMART anti-CD3 which is a humanized anti-CD3 IgG (Protein Design Lab); 5G1.1 which is a humanized anti-complement factor 5 (C5) antibody (Alexion Pharm); D2E7 which is a humanized anti-TNF-α antibody (CAT/BASF); CDP870 is a humanized anti-TNF-α Fab fragment (Ceiltech); IDEC-151 which is a primatized anti-CD4 IgG1 antibody (IDEC Pharm/SmithKline Beecham); MDX-CD4 which is a human anti-CD4 IgG antibody (Medarex/Eisai/Genmab); CDP571 which is a humanized anti-TNF-α IgG4 antibody (Celltech); LDP-02 which is a humanized anti-α4β7 antibody (LeukoSite/Genentech); OrthoClone OKT4A which is a humanized anti-CD4 IgG antibody (Ortho Biotech); ANTOVA™ which is a humanized anti-CD40L IgG antibody (Biogen); ANTEGREN™ which is a humanized anti-VLA-4 IgG antibody (Elan); and CAT-152 which is a human anti-TGF-$β_2$ antibody (Cambridge Ab Tech).

Other possible pharmaceutical compositions contemplated for production in accordance with the present invention, but are not limited to, albumin, α-1 antitrypsin, antithrombin III, collagen, factors VIII, IX, X (and the like), fibrinogen, hyaluronic acid, insulin, lactoferrin, protein C, erythropoietin (EPO), granulocyte colony-stimulating factor (G-CSF), granulocyte macrophage colony-stimulating factor (GM-CSF), tissue-type plasminogen activator (tPA), feed additive enzymes, somatotropin, and chymotrypsin. Other pharmaceutical compositions which may be produced as disclosed herein are disclosed in, for example, patents or pending patent applications which have incorporated in the present application by reference.

Heterologous protein(s) produced from cells in accordance with the present invention can be isolated from the cells or from the medium in which the cells are cultured using any useful art-recognized technique. Dialysis of the medium against dilute buffer or a superabsorbant material, followed by lyophilization, can be employed to remove the bulk of the low molecular weight components of the medium and to concentrate the heterologous protein. Alternatively, ultrafiltration or precipitation by saturation with salts such as sodium or ammonium sulfate can be used.

Once obtained in concentrated form, any standard technique, such as preparative disc gel electrophoresis, ion-exchange chromatography, gel filtration, size separation chromatography, isoelectric focusing and the like may be used to purify, isolate, and/or to identify the heterologous protein. Those skilled in the art may also readily devise affinity chromatographic means of heterologous protein purification, especially for those instances in which a binding partner of the heterologous protein is known, for example, antibodies.

Those skilled in the art will recognize, or be able to ascertain using no more than routine experimentation, many equivalents to the specific embodiments of the invention described herein. Such equivalents are intended to be encompassed by the following claims.

The present invention is further illustrated by the following examples, which are provided by way of illustration and should not be construed to limit the invention. The contents of all references, publications, patents and patent applications cited throughout the present application are hereby incorporated by reference in their entireties.

EXAMPLE 1

Stable Cell Line Promoter Assay

Figure 1:
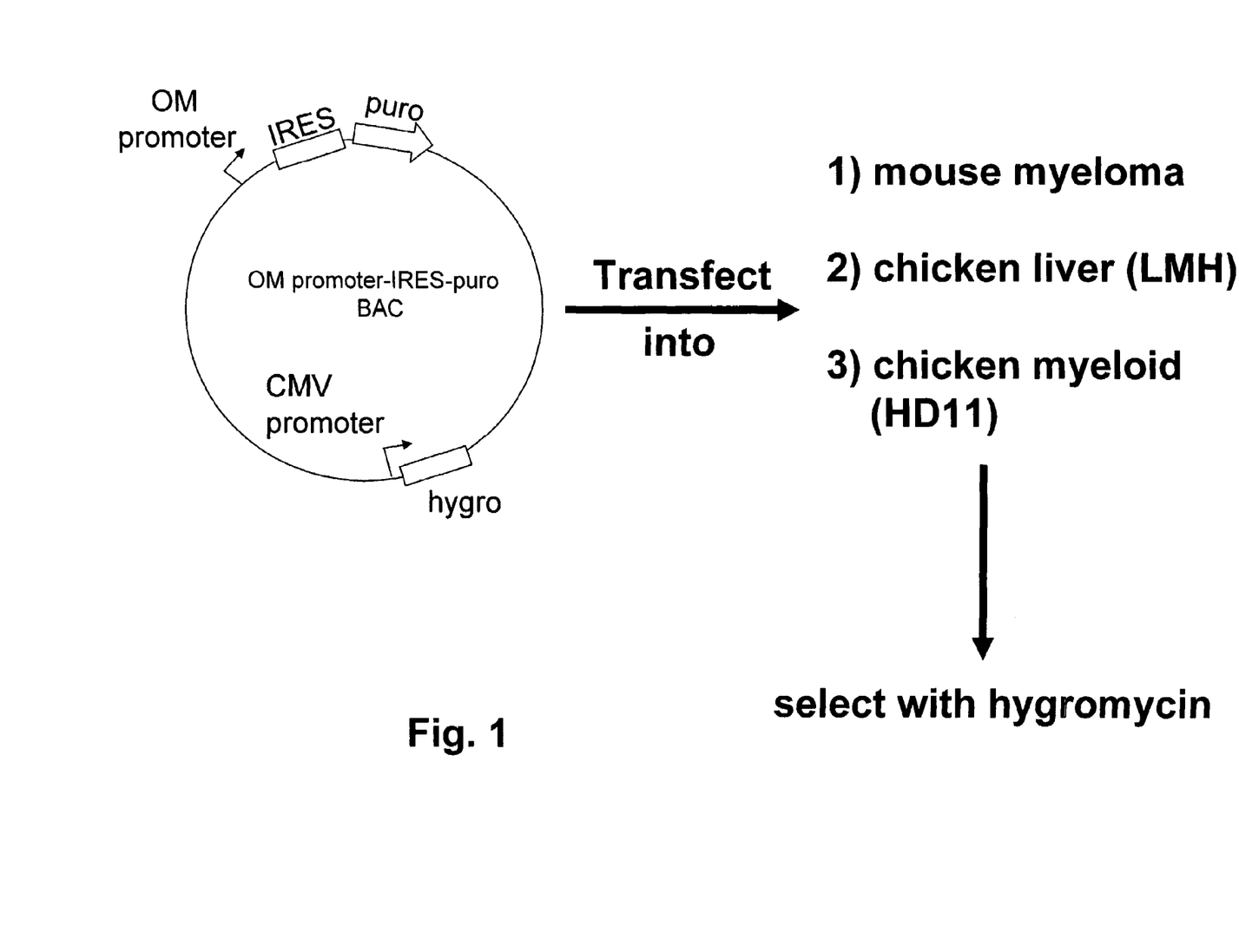
FIG. 1 shows an example of a vector that can be used in a promoter assay in a stable cell line and use of the vector to obtain an antibiotic (hygromycin) resistant cell line for the promoter assay.

The EPO coding sequence of the BAC clone OMC24-IRES1-EPO-ChromattB, disclosed in U.S. patent application Ser. No. 11/068,115, filed Feb. 28, 2005, the disclosure of which is incorporated in its entirety herein by reference, is removed and replaced with a puromycin-resistance coding sequence to produce OM promoter-IRES-puro BAC. See FIG. 1. The BAC is transfected into a certain stable cell line, for example, mouse myeloma, ATCC #CRL-1646; chicken myeloid cell line, HD11; or chicken liver cell line, ATCC #CRL-2117, and antibiotic resistant cells are selected for by growth in hygromycin-containing medium.

Figure 2:
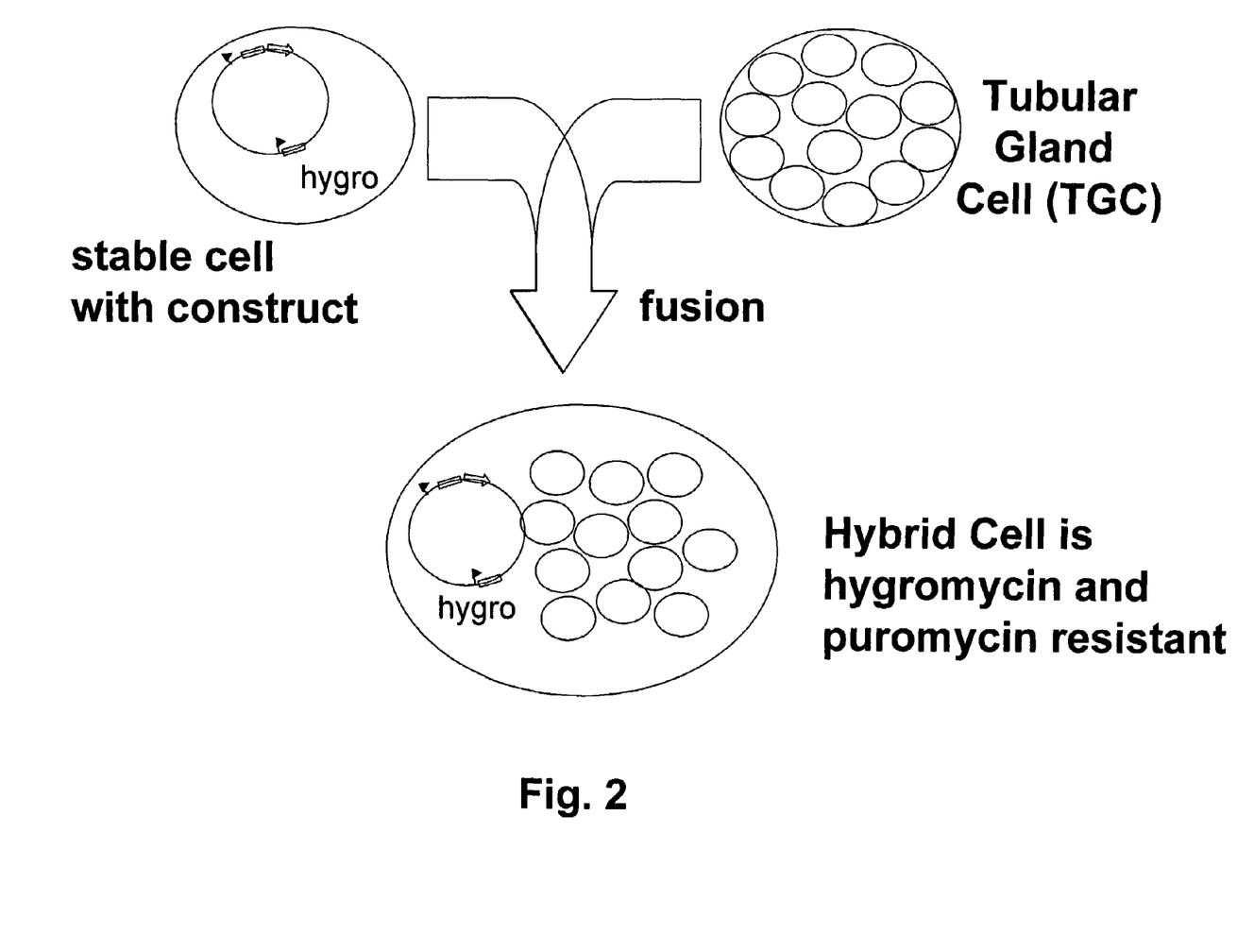
FIG. 2 shows the antibiotic (hygromycin) cell line of FIG. 1 fused with a tubular gland cell to produce a hybrid cell.

Antibiotic resistant cell lines containing the BAC are fused with TGCs obtained as disclosed herein using PEG and hybrid cells are selected for in puromycin containing medium (FIG. 2). In one embodiment, to fuse the TGCs with cells of a stable cell line, both are combined in a conical tube, centrifuged at 300×g for 5 min to remove medium, and mixed with polyethylene glycol (PEG) for several minutes (Roche Molecular Biochemicals fusion protocol, catalog item 783641). The mixture is then diluted with cell culture medium in a stepwise manner and centrifuged at 300×g for 5 min to remove PEG. The cell pellet is then resuspended in TGC medium (Dulbecco's modified eagle medium with 15% fetal calf serum, 1× pen/strep, $10^{-8}$M β-estradiol, $10^{-7}$M corticosterone, and $10^{-6}$M insulin). Hybrid cells which are resistant to hygromycin and puromycin are identified.

Figure 3:
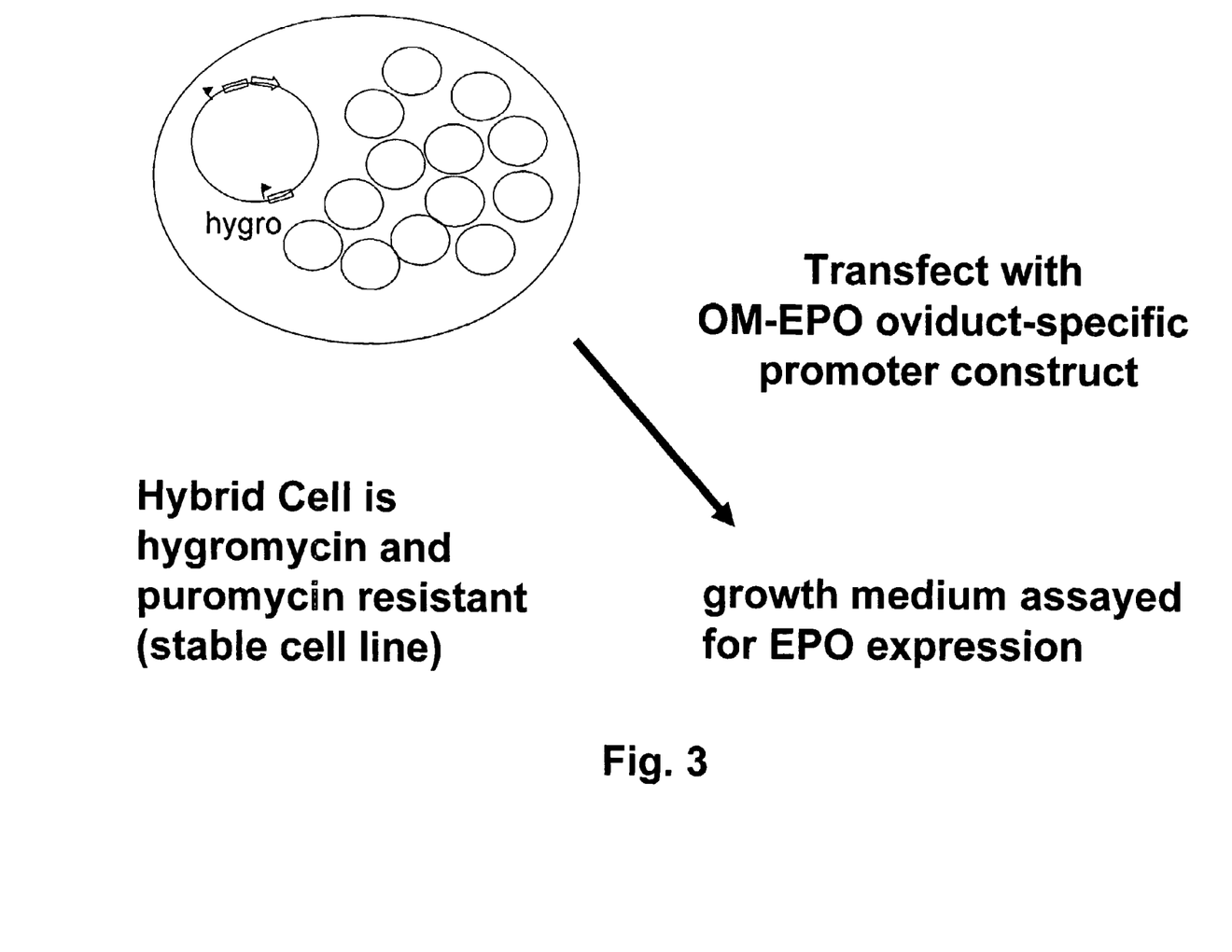
FIG. 3 shows transfection of the hybrid cell line of FIG. 2 with a cassette containing a coding sequence, in this case an erythropoietin coding sequence, operably lined to a promoter that is expressed in the oviduct (e.g., an oviduct specific promoter), in this case an ovomucoid promoter.
Figure 4:
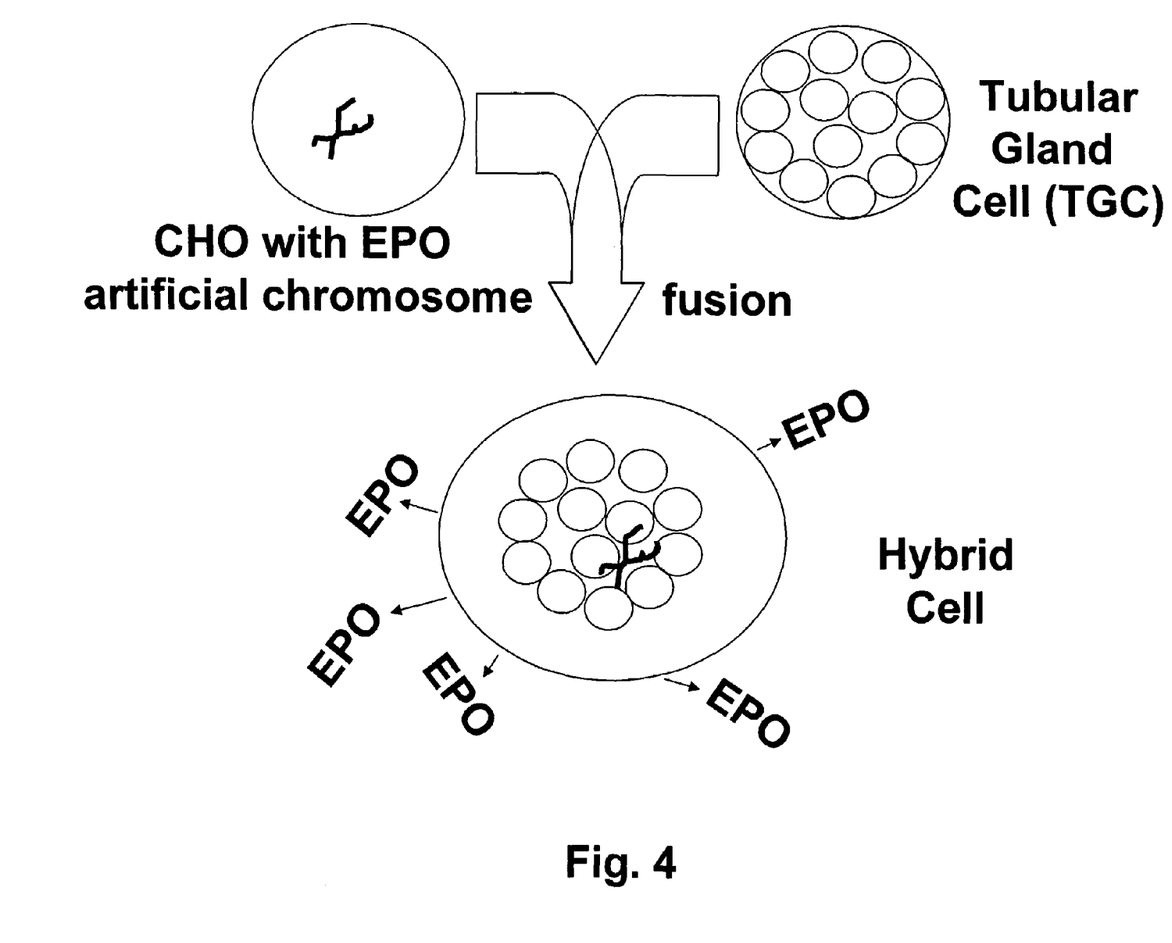
FIG. 4 shows production of a hybrid transient cell line that is useful for promoter activity assays. The figure shows erythropoietin being secreted from the cell which can be purified or can be quantified to determine the activity of the promoter driving EPO expression.

The hybrid hygromycin and puromycin resistant cells are used to test for expression of various TGC-specific promoters by transfection and ELISA. For example, as shown in FIG. 3, a hybrid cell line is transfected with a construct containing a portion of a magnum specific promoter operably linked to an erythropoietin coding sequence. The transfected cell line is cultured in growth medium which is assayed for EPO by ELISA to detect and/or quantify promoter activity of the magnum specific promoter.

EXAMPLE 2

Transient Cell Line Promoter Assay

A bacterial artificial chromosome (BAC) which contains the chicken ovomucoid promoter operably linked to a human erythropoietin (EPO) coding sequence has been constructed. This BAC was integrated into a mammalian artificial chromosome essentially as disclosed in Lindenbaum et al., 2004 and in U.S. patent application Ser. No. 11/362,064, filed Feb. 24, 2006, the disclosure of which is incorporated in its entirety herein by reference. Briefly, the BAC DNA was transfected into Chinese hamster ovary (CHO) cells containing a satellite DNA-based artificial chromosome (SATAC). Lambda integrase was co-transfected into the CHO cells, and site-specific integration of the BAC into the SATAC was catalyzed by the integrase. Cells which contained the integrated BAC constructs were selected for by growth on hygromycin-containing medium.

In the present example, CHO cells containing the SATAC with the integrated EPO coding sequence containing BAC are trypsinized and removed from the cell culture plates. Tubular gland cells (TGCs) are isolated from mature hen oviducts by enzymatic digestion of oviduct tissue samples with collagenase and dispase (Sanders and McKnight (1985) Chicken Egg White Genes: Multihormonal Regulation In A Primary Cell Culture System (1985) Endocrinology, January; 116(1):

398-405). About 1 of each of the CHO cells and TGCs obtained as disclosed herein are combined in a conical tube which is centrifuged at 300×g for 5 min and the medium is removed. The cells are maintained at 37° C.

The cell pellet is gently resuspended in 1 ml of 50% polyethylene glycol 1500 (PEG 1500) pre-warmed to 37° C. followed by incubation for three min at 37° C. (Roche Molecular Biochemicals fusion protocol, catalog item 783641). The mixture is diluted with 14 ml of cell culture medium pre-warmed to 37° C. in a stepwise manner (e.g., add 1 ml of medium and gently mix, add 3 ml more of medium and gently mix, then add 10 ml of medium and gently mix). The mixture is centrifuged at 300×g for 5 min and the supernatant is removed from the pellet. The cell pellet is then resuspended in 10 ml of TGC medium (Dulbecco's modified eagle medium with 15% fetal calf serum, 1× pen/strep, $10^{-8}$M β-estradiol, $10^{-7}$M corticosterone, and $10^{-6}$M insulin) pre-warmed to 37° C. and the cell suspension is plated to a 10 cm in diameter culture dish. The cells are maintained at 37° C. in 5% $CO_2$. At 24 and 48 hours post fusion, 1 ml aliquots of the cell medium are collected and assayed for expression of the EPO by ELISA to detect and/or quantify promoter activity.

EXAMPLE 3

Production of an Immortal Cell Line from Avian Oviduct Tissue

Epithelial adenoma tumors are isolated from a chicken oviduct and are finely minced into 1 to 2 mm pieces which are incubated in F12 medium with 0.8 mg/ml collagenase. The tissue is shaken at 37° C. for 30 minutes and triturated to generate cell clumps consisting of approximately 2 to 1000 cells. The clumps of cells are separated from red blood cells and cellular debris which is discarded. The clumps are suspended in pre-warmed F12 media, supplemented with 0.8 mg/ml collagenase and 1.0 mg/ml dispase, and incubated at 37° C. with shaking. Cell clumps are triturated every ten minutes to generate clumps consisting of about 2 to 100 cells. The cells are pelleted with low speed centrifugation and the resultant pellet is suspended in ice cold F12 which is filtered through a single layer of sterile surgical gauze tape to remove larger cell clumps. The cells are washed twice with ice cold F12, pelleted and resuspended in DMEM 15% FCS growth medium at an $OD_{600}$ of approximately 1.0.

The cells are grown in growth media at 5% $CO_2$ and 42° C. until the culture reaches confluency or until the diameter of cell clumps reach approximately one millimeter. Cell clumps and monolayers are subsequently treated with basal salts media which includes 0.8 mg/ml collagenase and 1.0 mg/ml dispase to produce a single cell suspension. Cells are pelleted and washed twice with basal salt media. After final wash, the cell pellet is suspended in growth media at a cell density of $1 \times 10^4$-$1 \times 10^6$ cells per milliliter.

Single cells are plated in each well of a 96 well plate and incubated in growth media. Immortal cell lines are identified which produce ovalbumin as determined by ELISA. Cells that express ovalbumin are passaged as needed to maintain viability. Each cell line is passaged a minimum of 20 times.

EXAMPLE 4

Production of an Immortal Cell Line from Avian Oviduct Tissue of a Transgenic Avian and Production of Heterologous Protein Transgenic chickens which produce eggs with interferon present in the egg white are disclosed in U.S. patent application Ser. No. 10/463,980, filed Jun. 17, 2003, the disclosure of which is incorporated in its entirety herein by reference. An interferon producing transgenic chicken is matured to five years of age. Oviduct tissue is removed from the chicken and several tumors are isolated. An immortal cell line is obtained from the tumors as described in Example 3.

Growth medium in which the immortal cell lines are passaged tests positive for interferon.

EXAMPLE 5

Production of an Immortal Cell Line from Avian Tubular Gland Cells

Freshly harvested chicken oviduct tissue is isolated from a healthy 40 week old chicken hen. The tissue is finely minced into small pieces approximately 1 mm in diameter. The tissue is shaken at 42° C. for 20 min and triturated to generate clumps each consisting of about 2 to 1000 cells. The clumps of cells are separated from red blood cells and cellular debris which is discarded and are then suspended in pre-warmed McCoy's 5A medium, supplemented with 0.8 mg/ml collagenase and 1.0 mg/ml dispase, and incubated at 42° C. with shaking. The cell clumps are triturated every ten minutes to generate clumps consisting of about 2 to 100 cells. The cells are then collected by low speed centrifugation. The resultant pellet is suspended in ice cold McCoy's 5A medium and filtered through a single layer of sterile surgical gauze tape to remove large clumps. The cells are then washed 2 times in McCoy's 5A medium.

Cells are centrifuged, counted, and resuspended in serum-free RPMI medium rat 1640 containing 0.4 mg/ml Aroclor 1254-induced S9 liver extracts (Moltox, Boone, N.C.), 0.23 mM NADP, 0.28 mM glucose 6-phosphate, 0.45 mM $MgCl_2$, 0.45 mM KCl, and 200 mM Tris.HCl (pH 7.5) plus 50 uM N-methyl-N'-nitro-N-nitrosoguanidine (MNNG).

The cells are treated for 2 hours at 42° C. After treatment, the cells are resuspended in complete McCoy's 5A medium and reseeded. MNNG-resistant cell lines are established by two successive treatments with 5 uM MNNG and 25 uM $O^6$-benzylguanine. Each round of treatment is performed after cells surviving the prior round of treatment have recovered exponential growth. Single-cell clones are obtained by limiting dilution. Each clone is grown to confluency in a well of a six well plate. Each cell line is passaged a minimum of 20 times.

EXAMPLE 6

Transformation of an Avian Tubular Gland Cell Immortal Cell Line and Production of Heterologous Protein An immortal cell line of Example 3 or Example 5 is transformed with an OMC24-attB-IRES-G-CSF vector with a neomycin resistance coding sequence inserted downstream of the ovomucoid transcription initiation start site such that both the G-CSF and neomycin resistance are expressed. OMC24-attB-IRES-G-CSF is disclosed in U.S. patent application Ser. No. 10/940,315, filed Sep. 14, 2004 and U.S. patent application Ser. No. 10/856,218, filed May 28, 2004. The disclosure of each of these two patent applications is incorporated herein in its entirety by reference.

OMC24-attB-IRES-G-CSF-Neo is transfected into actively growing cell lines produced as described in Example 3 and Example 5. For each cell line, 0.2 ml of cells, which have been washed in OptiMem medium, and 0.6 ml of Opti- Mem medium plus 10 nm estrogen, 100 nm corticosterone and 1 um insulin (OptiMem) are added to each of six wells in a six well multiwell plate.

For each transfection, 5 ul of Dmrie C (Invitrogen, Inc.) and 95 ul of OptiMem is added to a polycarbonate tube. Approximately 20 ug of the OMC24-attB-IRES-G-CSF-Neo vector in 100 ul of OptiMen is mixed into the Dmrie solution by pipetting. The DNA-lipid mixture is let to stand for about 15 min at room temperature in the hood.

200 ul of the lipid/DNA/OptiMem mix is added to the 0.8 mls of cells in each well for a total of 1 ml volume. Incubate at 42° C., 5% $CO_2$ for at least 5 to 6 hours.

2 mls of 15% FCS DMEM plus 10 nm estrogen, 100 nm corticosterone and 1 um insulin high glucose with no phenol red with 2× neomycin is added to the transfection medium. The cells are incubated for 24 hours followed by a change medium to fresh 10% FCS DMEM hi glucose plus neomycin with no phenol red followed by 24 hours of incubation. The cells are diluted and grown for an additional 24 hour at which time individual colonies are picked, transferred to individual wells of a six well plate and grown to confluency. For each cell line which is passaged a minimum of 20 times, the growth medium tests positive for G-CSF.

While this invention has been described with respect to various specific examples and embodiments, it is to be understood that the invention is not limited thereto and that it can be variously practiced with the scope of the following claims.

What is claimed is:

1. A method comprising culturing under suitable nutrient conditions a hybrid cell comprising an avian tubular gland cell (TGC) fused to an immortal cell, wherein said hybrid cell comprises an exogenous nucleic acid sequence encoding a protein operably linked to an oviduct specific promoter.

2. The method of claim 1 wherein the hybrid cell is sustainable in culture for at least ten or more passages.

3. The method of claim 1 wherein the hybrid cell is sustainable in culture for at least twenty or more passages.

4. The method of claim 1, wherein the protein is a human protein.

5. The method of claim 1, wherein the protein is a marker protein.

6. The method of claim 1 wherein the oviduct specific promoter is selected from the group consisting promoters for ovalbumin, ovomucoid, conalbumin, ovomucin and lysozyme proteins.

7. The method of claim 1, wherein the tubular gland cell and the immortal cell are fused using polyethylene glycol.

8. The method of claim 1, wherein the hybrid cell is of a hybrid cell line.

9. A method comprising: i) culturing under suitable nutrient conditions a hybrid cell comprising an avian tubular gland cell (TGC) fused to an immortal cell, wherein said hybrid cell comprises an exogenous nucleic acid sequence encoding a therapeutic protein operably linked to an oviduct specific promoter, wherein the hybrid cell secretes the therapeutic protein; and ii) isolating the therapeutic protein.

10. The method of claim 9 wherein the hybrid cell is sustainable in culture for at least ten or more passages.

11. The method of claim 9 wherein the hybrid cell is sustainable in culture for at least twenty or more passages.

12. The method of claim 9 wherein the oviduct specific promoter is a promoter for ovomucin protein.

13. The method of claim 9 wherein the oviduct specific promoter is a promoter for ovalbumin protein.

14. The method of claim 9 wherein the oviduct specific promoter is a promoter for ovomucoid protein.

15. The method of claim 9 wherein the oviduct specific promoter is a promoter for lysozyme protein.

16. The method of claim 9 wherein the oviduct specific promoter is a promoter for conalbumin protein.

17. The method of claim 9 wherein the therapeutic protein is selected from the group consisting of antibodies, cytokines, fusion proteins, growth factors, enzymes, interferons, granulocyte-colony stimulating factors, and erythropoietins.

18. The method of claim 9, wherein the hybrid cell is of a hybrid cell line.

* * * * *